US00PP21505P2

(12) United States Plant Patent
Hooijman

(10) Patent No.: US PP21,505 P2
(45) Date of Patent: Nov. 16, 2010

(54) ***HYPERICUM* PLANT NAMED 'ESM CHOCOLA'**

(50) Latin Name: *Hypericum hybrida*
Varietal Denomination: Esm Chocola

(75) Inventor: Aloysius A. J. Hooijman, Aalsmeer (NL)

(73) Assignee: Esmeralda Breeding B.V., Aaslmeer (NL)

( * ) Notice: Subject to any disclaimer, the term of this patent is extended or adjusted under 35 U.S.C. 154(b) by 0 days.

(21) Appl. No.: 12/587,465

(22) Filed: Oct. 7, 2009

(51) Int. Cl.
*A01H 5/00* (2006.01)

(52) U.S. Cl. ..... Plt./442

(58) Field of Classification Search ..... Plt./442
See application file for complete search history.

*Primary Examiner*—Kent L Bell
(74) *Attorney, Agent, or Firm*—C. A. Whealy

(57) ABSTRACT

A new and distinct cultivar of *Hypericum* plant named 'Esm Chocola', characterized by its upright, symmetrical and long flowering stems; moderately vigorous growth habit; uniform and freely flowering habit; uniform and high density of fruits; spherical brown-colored fruits; and excellent post-production longevity.

1 Drawing Sheet

Botanical designation: *Hypericum hybrida.*
Cultivar denomination: 'Esm Chocola'.

BACKGROUND OF THE INVENTION

The present invention relates to a new and distinct cultivar of *Hypericum* plant, botanically known as *Hypericum hybrida* and hereinafter referred to by the name 'Esm Chocola'.

The new *Hypericum* plant is a product of a planned breeding program conducted by the Inventor in El Quinche, Pichincha, Ecuador. The objective of the breeding program is to create new *Hypericum* plants with good density, compact inflorescences and good productivity.

The new *Hypericum* plant originated from a cross-pollination in August, 2003 in El Quinche, Pichincha, Ecuador of a proprietary selection of *Hypericum hybrida* identified as Line 124, not patented, as the female, or seed parent with a proprietary selection of *Hypericum hybrida* identified as Line 113, not patented, as the male, or pollen, parent. The new *Hypericum* plant was discovered and selected by the Inventor as a single flowering plant within the progeny of the stated cross-pollination in a controlled environment in El Quinche, Pichincha, Ecuador in June, 2004.

Asexual reproduction of the new cultivar by vegetative cuttings in El Quinche, Pichincha, Ecuador, since July, 2004, has shown that the unique features of this new *Hypericum* plant are stable and reproduced true to type in successive generations.

SUMMARY OF THE INVENTION

Plants of the new *Hypericum* have not been observed under all possible environmental conditions. The phenotype may vary somewhat with variations in environment such as temperature and light intensity without, however, any variance in genotype.

The following traits have been repeatedly observed and are determined to be the unique characteristics of 'Esm Chocola'. These characteristics in combination distinguish 'Esm Chocola' as a new and distinct cultivar of *Hypericum:*

1. Upright, symmetrical and long flowering stems.
2. Moderately vigorous growth habit.
3. Uniform and freely flowering habit; uniform and high density of fruits.
4. Spherical brown-colored fruits.
5. Excellent post-production longevity.

Plants of the new Hypericum differ from plants of the female parent selection in the following characteristics:

1. Plants of the new *Hypericum* are shorter than plants of the female parent selection.
2. Plants of the new *Hypericum* flower later than plants of the female parent selection.
3. Plants of the new *Hypericum* and the female parent selection differ in fruit shape and color as plants of the female parent selection have ovoid red-colored fruits.
4. Plants of the new *Hypericum* have longer post-production longevity than plants of the female parent selection.

Plants of the new *Hypericum* differ from plants of the male parent selection in the following characteristics:

1. Plants of the new *Hypericum* are shorter than plants of the male parent selection.
2. Plants of the new *Hypericum* and the male parent selection differ in fruit shape and color as plants of the male parent selection have ovoid red-colored fruits.
3. Plants of the new *Hypericum* have longer post-production longevity than plants of the male parent selection.

Plants of the new *Hypericum* can be compared to plants of the *Hypericum* 'Excellent Flair', not patented. In side-by-side comparisons in El Quinche, Pichincha, Ecuador, plants of the new *Hypericum* differed from plants of 'Excellent Flair' in the following characteristics:

1. Plants of the new *Hypericum* were shorter, broader and had shorter internodes than plants of 'Excellent Flair'.
2. Plants of the new *Hypericum* had stronger stems than plants of 'Excellent Flair'.
3. Plants of the new *Hypericum* flowered later than plants of 'Excellent Flair'.
4. Plants of the new *Hypericum* had spherical fruits whereas plants of 'Excellent Flair' had ovoid fruits.

BRIEF DESCRIPTION OF THE PHOTOGRAPHS

The accompanying colored photographs illustrate the overall appearance of the new *Hypericum* plant, showing the colors as true as it is reasonably possible to obtain in colored reproductions of this type. Colors in the photographs may differ slightly from the color values cited in the detailed botanical description which accurately describe the actual colors of the new *Hypericum* plant.

The photograph at the top left of the sheet comprises a side perspective view of a typical stem of 'Esm Chocola' with mature fruits.

The photograph at the bottom left of the sheet is a close-up view of typical fruits of 'Esm Chocola'.

The photographs at the top right and center right of the sheet are close-up views of typical fruits.

The photograph at the bottom right of the sheet is a close-up view of the upper and lower surfaces of typical leaves.

DETAILED BOTANICAL DESCRIPTION

Plants used for the aforementioned photographs and following description were grown under conditions which closely approximate commercial production conditions in an outdoor nursery in El Quinche, Pichincha, Ecuador. During the production of the plants, day temperatures ranged from 11° C. to 28° C., night temperatures ranged from 5° C. to averaged 11° C. Plants were pinched four weeks after planting and were six months old when the photographs and the description were taken. In the following description, color references are made to The Royal Horticultural Society Colour Chart, 2001 Edition, except where general terms of ordinary dictionary significance are used.

Botanical classification: *Hypericum hybrida* 'Esm Chocola'.

Parentage:

*Female, or seed, parent.*—Proprietary selection of *Hypericum hybrida* identified as Line 124, not patented.

*Male, or pollen, parent.*—Proprietary selection of *Hypericum hybrida* identified as Line 113, not patented.

Propagation:

*Type cutting.*—Vegetative cuttings.

*Time to initiate roots.*—About seven to ten days at 22° C. to 30° C.

*Time to produce a rooted young plant.*—About four to five weeks at 22° C. to 30° C.

*Root description.*—Medium thickness, fibrous; color close to 200D.

*Rooting habit.*—Freely branching; dense.

Plant description:

*Form.*—Perennial woody shrub typically grown as a cut flower-type *Hypericum*; upright, symmetrical and long flowering stems; moderately vigorous growth habit; basally branching habit with about six flowering stems developing per plant per year.

*Plant height.*—About 90 cm.

*Plant width (spread).*—About 40 cm.

*Lateral branch description.*—Length: About 85 cm. Diameter: About 6 mm. Internode length: About 4 cm. Strength: Strong. Texture: Smooth, glabrous. Color: Close to 166A to N170A.

Foliage description:

*Arrangement.*—Opposite, simple; sessile.

*Length.*—About 6 cm.

*Width.*—About 4 cm.

*Shape.*—Ovate.

*Apex.*—Obtuse to retuse.

*Base.*—Truncate.

*Margin.*—Entire.

*Texture, upper and lower surfaces.*—Glabrous; leathery; rugose.

*Venation pattern.*—Pinnate.

*Color.*—Developing leaves, upper surface: Close to 137A to 139A. Developing leaves, lower surface: Close to 146B. Fully expanded leaves, upper surface: Close to 139A; venation, close to 145B. Fully expanded leaves, lower surface: Close to 147B; venation, 146D.

Flower description:

*Flower arrangement and shape.*—Bright yellow-colored single flowers arranged in terminal compound umbels; freely flowering habit with about nine flowers per inflorescence; flowers face mostly upright.

*Fragrance.*—Moderately fragrant.

*Natural flowering season.*—Year-round in Ecuador; plants begin flowering about 19 weeks after planting.

*Flower longevity.*—Flowers last about three to four days on the plant; flowers not persistent.

*Flower buds.*—Length: About 1 cm. Diameter: About 8 mm. Shape: Globose. Color: Close to 15A, towards the base, close to 10A.

*Inflorescence size.*—Length: About 12 cm. Diameter: About 12 cm.

*Flowers.*—Diameter: About 3 cm. Depth (height): About 1.4 cm.

*Petals.*—Quantity/arrangement: Five in a single whorl. Length: About 1.3 cm. Width: About 1 cm. Shape: Oval. Apex: Obtuse. Base: Attenuate. Margin: Entire. Texture, upper and lower surfaces: Glabrous, smooth; papery. Aspect: Incurved, concave. Color: When opening, upper surface: Close to 14B. When opening, lower surface: Close to 12A. Fully opened, upper surface: Close to 14A; color becoming close to 17A with development. Fully opened, lower surface: Close to 9A.

*Sepals.*—Quantity/arrangement: Five in a single whorl; three larger than the other two. Length: About 7 mm to 8 mm. Width: About 4 mm to 6 mm. Shape: Ovate to elliptic. Apex: Acute. Base: Attenuate. Margin: Entire. Texture, upper and lower surfaces: Glabrous, smooth. Color: When opening, upper surface: Close to 146A; towards the base, close to 53B. When opening, lower surface: Close to 146C; towards the base, close to N34A. Fully opened, upper surface: Close to 137A. Fully opened, lower surface: Close to 146A.

*Peduncles.*—Strength: Strong. Length: About 5 cm. Diameter: About 6 mm. Texture: Smooth, glabrous. Color: Close to 182B to N167B.

*Pedicels.*—Strength: Strong. Length: About 1.1 cm. Diameter: About 2 mm. Aspect: About 41° from the stem axis. Texture: Smooth, glabrous. Color: Close to 187B.

*Reproductive organs.*—Stamens: Quantity per flower: About 130. Anther shape: Reniform. Anther length: About 1 mm. Anther color: Close to 14A. Pollen amount: Abundant. Pollen color: Close to 14B. Pistils: Quantity per flower: Single pistil with three stigmas. Pistil length: About 1 cm. Stigma shape: Circular. Stigma color: Close to 59A. Style length: About 5 mm. Style color: Close to 151D. Ovary color: Close to 150B.

*Fruits.*—Length: About 1.1 cm. Diameter: About 1.1 cm. Shape: Roughly spherical. Texture: Smooth, glabrous. Post-production longevity: Fruits last for about 15 days as a cut stem. Color: Close to 183A; towards the base, close to 144A.

*Seeds.*—Length: About 0.1 mm. Diameter: About 0.03 mm. Color: Close to 200C.

Disease/pest resistance: Plants of the new *Hypericum* have not been noted to be resistant to pathogens and pests common to *Hypericum.*

Weather/temperature tolerance: Plants of the new *Hypericum* have been observed to tolerate wind, rain and temperatures ranging from about 5° C. to about 30° C.

It is claimed:

1. A new and distinct *Hypericum* plant named 'Esm Chocola' as illustrated and described.

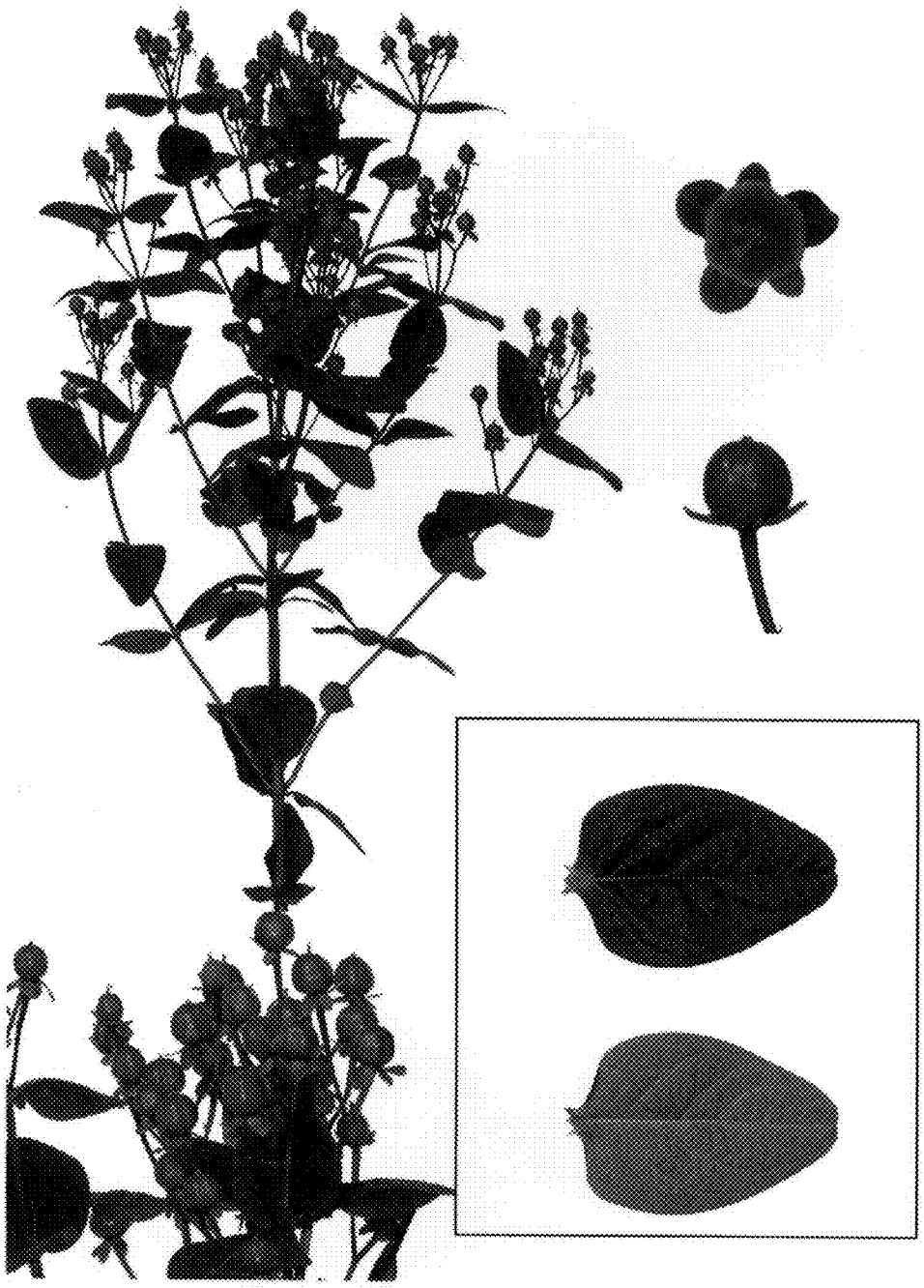

* * * * *